United States Patent [19]
Krueger

[11] Patent Number: 5,904,695
[45] Date of Patent: *May 18, 1999

[54] APPARATUS FOR ATTACHMENT OF HEART VALVE HOLDER TO HEART VALVE PROSTHESIS

[75] Inventor: Kurt D. Krueger, Stacy, Minn.

[73] Assignee: St. Jude Medical, Inc., St. Paul, Minn.

[*] Notice: This patent issued on a continued prosecution application filed under 37 CFR 1.53(d), and is subject to the twenty year patent term provisions of 35 U.S.C. 154(a)(2).

[21] Appl. No.: 08/882,858

[22] Filed: Jun. 26, 1997

Related U.S. Application Data

[62] Division of application No. 08/528,361, Sep. 14, 1995, Pat. No. 5,695,503.

[51] Int. Cl.⁶ .................................................... A61B 17/08
[52] U.S. Cl. ................... 606/151; 606/151; 623/2
[58] Field of Search .............................. 606/151; 623/1, 623/2

[56] References Cited

U.S. PATENT DOCUMENTS

| | | | |
|---|---|---|---|
| 3,587,115 | 6/1971 | Shiley | 3/1 |
| 3,781,969 | 1/1974 | Anderson | 29/445 |
| 3,828,787 | 8/1974 | Anderson et al. | 128/303 |
| 4,532,659 | 8/1985 | Kaster | 623/2 |
| 4,683,883 | 8/1987 | Martin | 128/303 |
| 4,932,965 | 6/1990 | Phillips | 623/2 |
| 5,197,979 | 3/1993 | Quintero et al. | 623/2 |
| 5,425,705 | 6/1995 | Evard et al. | 604/28 |
| 5,433,700 | 7/1995 | Peters | 604/4 |
| 5,480,425 | 1/1996 | Ogilive | 623/2 |
| 5,578,076 | 11/1996 | Krueger et al. | 623/2 |

FOREIGN PATENT DOCUMENTS

| | | |
|---|---|---|
| WO 94/18881 | 9/1994 | WIPO . |
| WO 95/15715 | 6/1995 | WIPO . |

*Primary Examiner*—Michael Buiz
*Assistant Examiner*—Tina T. D. Pham
*Attorney, Agent, or Firm*—Hallie A. Finucane, Esq.; Westman, Champlin & Kelly, P.A.

[57] ABSTRACT

A device for engaging a heart valve prosthesis during implantation includes a mechanism for attaching the device to the heart valve prosthesis. The heart valve prosthesis includes a circular valve body having an annulus with a substantially annular aperture therein. At least one movable occluder is carried in the annulus and is movable between an open position and a closed position. The occluder is carried on a strut coupled to a valve body. The attachment mechanism includes a member which couples to the strut, thereby affixing the device to the heart valve prosthesis. The attachment mechanism may be actuated to disengage the heart valve prosthesis.

9 Claims, 4 Drawing Sheets

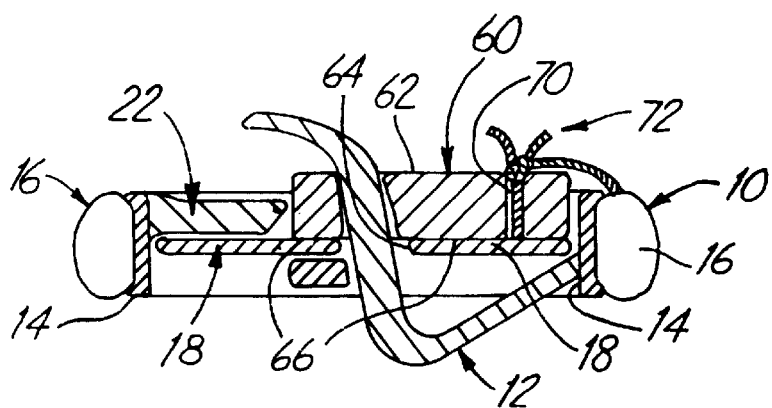
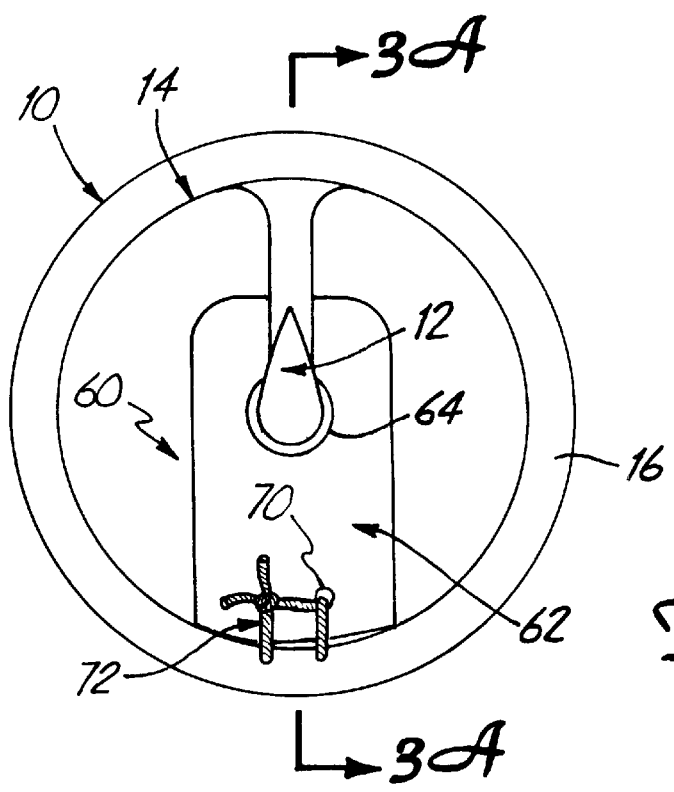

APPARATUS FOR ATTACHMENT OF HEART VALVE HOLDER TO HEART VALVE PROSTHESIS

This is a Divisional of application Ser. No. 08/528,361, filed Sep. 14, 1995 now U.S. Pat. No. 5695,803.

The present invention relates to devices for implanting heart valve prostheses. More specifically, the invention relates to attachment of a heart valve holder to a heart valve prosthesis.

BACKGROUND OF THE INVENTION

Holders for holding heart valve prostheses during implantation are known. They are used for positioning, holding, supporting and presenting the valve during surgery. U.S. Pat. No. 3,828,787, issued Aug. 13, 1974, to Anderson et al., entitled COLLET FOR HOLDING HEART VALVE, shows a heart valve holder carried on a distal end of an elongated handle. U.S. Pat. No. 4,932,965, issued Jun. 12, 1990, to Phillips, entitled ARTIFICIAL VALVE, AND NEEDLE AND SUTURE HOLDER AND METHOD OF USING SAME, shows another heart valve holder in which the valve is held against distal ends of a pair of elongated legs during implantation.

Typically, heart valve replacement surgery is an involved procedure in which a sternotomy or thoracotomy is performed and the chest cavity of the patient must be widely opened to provide access to the patient's heart. This provides a surgeon with direct, unobstructed access to the heart. However, this procedure requires a prolonged period to recover from the trauma suffered to the upper torso.

Recently, a procedure has been developed wherein open heart surgery is performed through trocars placed in small incisions between ribs of the patient. This is described in International Publication No. WO 95/15715, entitled DEVICES AND METHODS FOR INTRACARDIAC PROCEDURES; U.S. Pat. No. 5,433,700, issued Jul. 18, 1995, to Peters, entitled METHOD FOR INTRALUMINALLY INDUCING CARDIOPLEGIC ARREST AND CATHETER FOR USE THEREIN; and U.S. Pat. No. 5,425,705, issued Jun. 20, 1995, to Evard et al., entitled THORACOSCOPIC DEVICES AND METHODS FOR ARRESTING THE HEART; and International Publication No. WO 94/18881, entitled METHOD FOR PERFORMING THORASCOPIC CARDIAC BYPASS PROCEDURES. In this procedure, elongated tools are used to operate on the heart through the trocars. As discussed in Publication No. WO 95/15715, this procedure can be used during heart valve replacement. When a heart valve prosthesis is inserted through a trocar, extreme care has to be taken for protecting the occluders in the valve, and once inserted, it becomes desirable to change the orientation of the valve prior to implementation to simplify the suturing of the heart valve prosthesis in place.

The trocar results in minimal rib spreading and does not involve the significant chest trauma associated with traditional open heart surgery. One advantage of this procedure is that the recovery period can be reduced significantly. Unfortunately, mechanical heart valves and the associated assembly used for implantation are large relative to the intercostal space between the ribs and are difficult to fit therethrough. Further, the heart valve holder must be securely attached to the heart valve prosthesis and yet be easily removed once the valve has been attached to the heart tissue annulus.

SUMMARY OF THE INVENTION

A device for engaging a heart valve prosthesis during implantation includes a mechanism for attaching the device to the heart valve prosthesis. The heart valve prosthesis includes a circular valve body having an annulus with a substantially annular aperture therein. At least one movable occluder is carried in the annulus and is movable between an open position and a closed position. The occluder is carried on at least one elongated strut having a portion which extends in a direction parallel with an axis of the heart valve prosthesis. The attachment mechanism includes a member which couples to the strut, thereby affixing the device to the heart valve prosthesis at the strut. The member is selectively removable from the strut, thereby releasing the device from the strut. In one embodiment, an elongated handle couples to the device and extends away from the device in a plane generally parallel with a plane formed by the annulus of the heart valve prosthesis.

BRIEF DESCRIPTION OF THE DRAWINGS

FIG. 3A is cross sectional view of the heart valve holder shown in FIG. 3B taken along line 3A—3A in accordance with another embodiment engaged with a heart valve prosthesis.

FIG. 3B is a top plan view of the heart valve holder and heart valve prosthesis of FIG. 3A.

DETAILED DESCRIPTION OF THE PREFERRED EMBODIMENTS

The invention relates to attachment of a prosthetic heart valve holder to a heart valve prosthesis. The holder is used to position the heart valve prosthesis during implantation. In one embodiment, this implantation is through minimally invasive surgery, such as when performed through a small trocar or similar device. The holder and valve are carried at the distal end of a handle which extends perpendicular to the axis of the valve annulus during insertion through the trocar. Reference is made to copending application Ser. No. 08/526,530 filed on Sep. 11, 1995, entitled LOW PROFILE MANIPULATORS FOR HEART VALVE PROSTHESES. For purposes of this description of the invention, the holder and attachment mechanism will be described generally. The holder and attachment mechanism may be used with any appropriate heart valve prosthesis including heart valve prostheses which are available from Medtronic, Inc., Minneapolis, Minn.; Shiley, Inc., Irving, Calif.; and Omniscience Medical Inc., Grove Heights, Minn. In general, heart valve prostheses depicted herein are shown in a generic form and the scope of the present invention is intended to cover variations required to adapt the holder and attachment mechanism to different heart valve prostheses.

Figure 1:
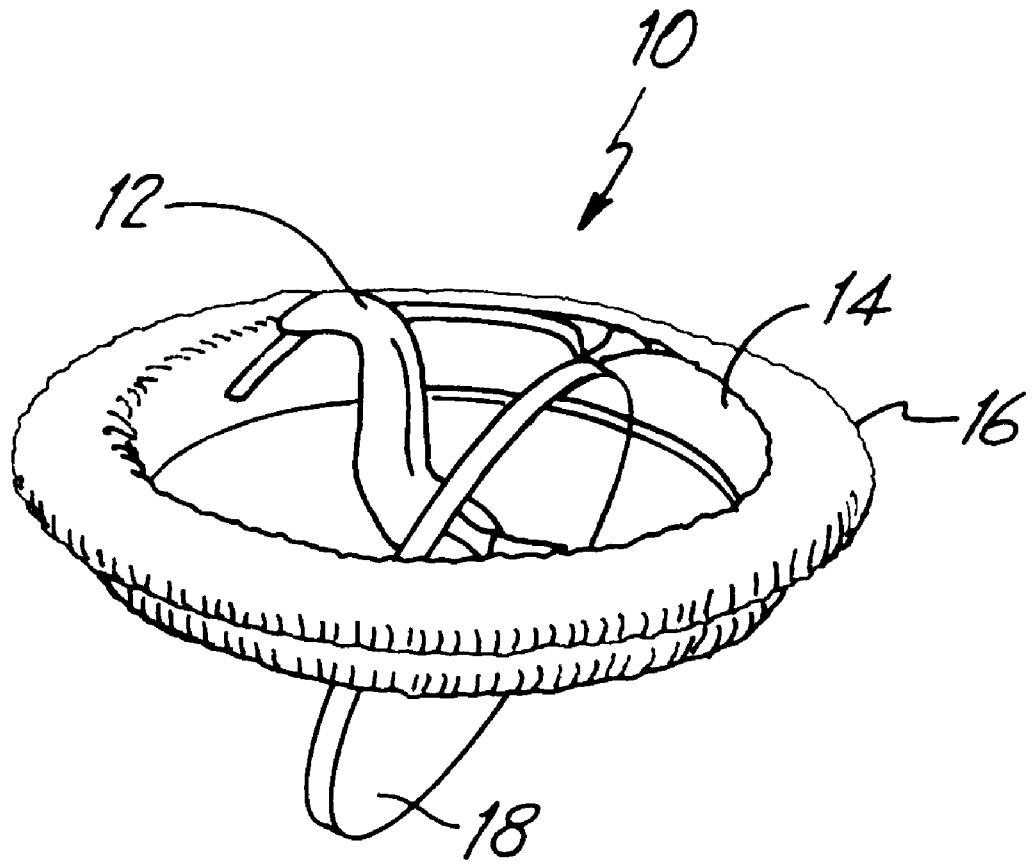
FIG. 1 is a prospective view of a prior art heart valve for use with a holder in accordance with the present invention.

FIG. 1 is a prospective view of a heart valve prosthesis 10. Heart valve prosthesis 10 is available from Medtronic, Inc. of Minneapolis, Minn., and is illustrative of a type of heart valve prosthesis which includes a primary strut 12. Primary strut 12 couples to heart valve prosthesis body 14. Heart valve body 14 forming a substantially round annulus for blood flow therethrough. A suture cuff 16 is attached to body 14 and is used to attach valve 10 to the patient's heart. An occluder 18 is positioned in the annulus formed by orifice body 14 and is guided by primary strut 12. Occluder 18 is movable between an open position shown in FIG. 1 and a closed position. Primary strut 12 provides a guiding mechanism for occluder 18 and is formed of an elongated member, a portion of which extends parallel to the axis of valve 10. Other examples of heart valve prostheses which use a strut configuration are shown in U.S. Pat. Nos. 3,828,787; 3,781,969; and 4,532,659, for example.

It has been discovered that the strut is a useful attachment point for attaching a heart valve holder to a heart valve prosthesis. The strut is particularly useful in attaching a heart valve holder having a low profile design to the heart valve prosthesis. Such a low profile design is well suited for use with the minimally invasive techniques described in International Publication No. WO 95/15715.

Figure 2A:
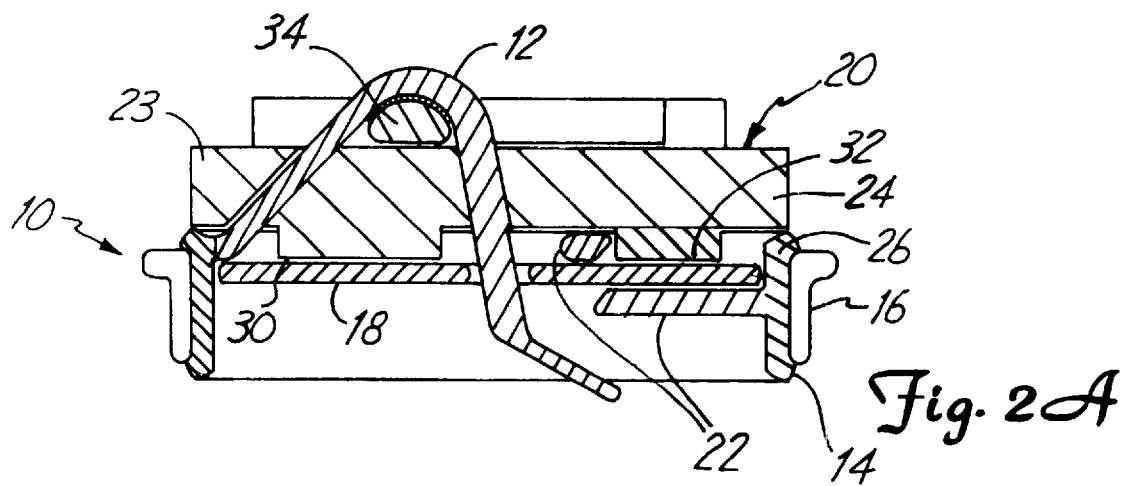
FIG. 2A is a side cross sectional view of the heart valve holder and heart valve shown in FIG. 2B taken along line 2A—2A in accordance with one embodiment of the present invention engaged with a heart valve prosthesis.
Figure 2B:
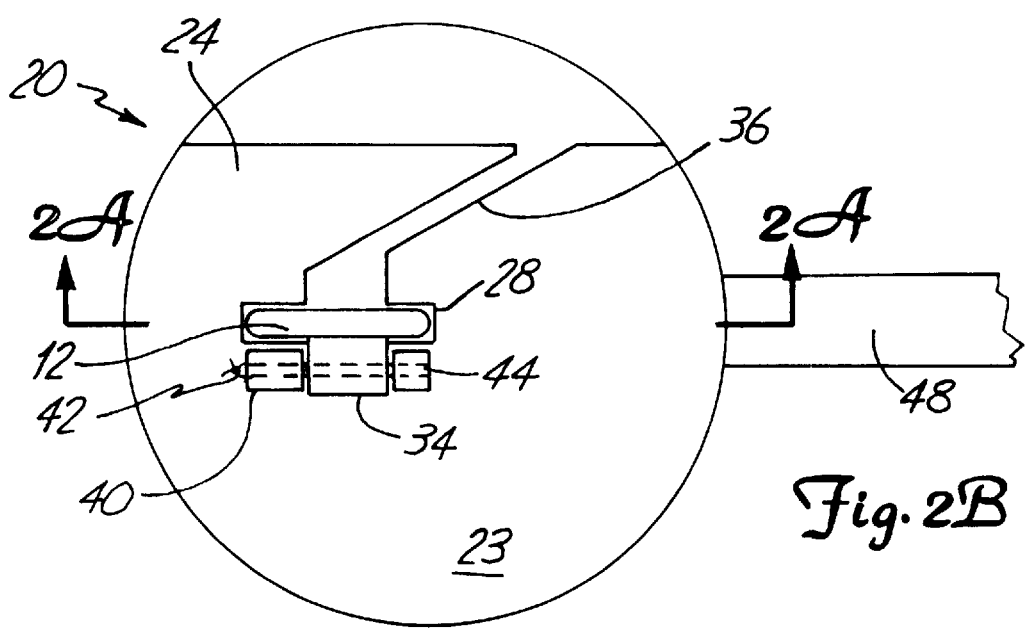
FIG. 2B is a top plan view of the heart valve holder of FIG. 2A.

FIG. 2A is a side cross sectional view of valve holder 20 in accordance with one embodiment of the present invention engaged with heart valve prosthesis 10 of FIG. 1. Valve prosthesis 10 includes valve secondary struts 22 which are not visible in FIG. 1. FIG. 2B is a top plan view of holder 20 showing primary strut 12 protruding therethrough.

Holder 20 includes holder body 24 adapted to fit within rim 26 of heart valve prosthesis body 14. Holder body 24 includes a strut opening 28 for receiving primary strut 12 therethrough. Occluder engaging surfaces 30 and 32 extend from heart valve holder body 24 and engage occluder 18 as shown substantially in FIG. 2A. Surfaces 30 and 32 maintain occluder 18 in a closed position. A locking bar 34 fits through primary strut 12 between primary strut 12 and holder body 24. Locking bar 34 is coupled to holder body 24 through spring loaded locking bar cantilever 36. Holder 20 connects heart valve prosthesis 10 at the interface between body 24 and rim 26 of heart valve prosthesis body 14 and is secured by the interface between locking bar 34 and primary strut 12. Connection flange 40 extends above surface 23 on holder body 24 and receives sutures 42 therethrough. Sutures 42 extend through suture hole 44 and through locking bar 34 to secure locking bar 34 in the locked position shown in FIG. 2B.

During implantation, a surgeon manipulates valve 10 using elongated handle 48 which extends in a direction generally parallel with the plane of valve 10 and perpendicular to the axis of valve 10. The surgeon sutures valve 10 to the heart tissue annulus using suture cuff 16. Following attachment of valve 10 to the heart tissue annulus, holder 20 is removed by cutting suture 42, thus allowing cantilever 36 to disengage locking bar 34 from primary strut 12. Following disengaging of locking bar 34 from primary strut 12, holder 20 may be lifted from valve 10, thereby allowing occluder 18 to pivot freely on primary strut 12. During implantation, occluder 18 is held in a substantially closed position and protected by the heart valve prosthesis body 14 and holder 20.

FIG. 3A is a side cross sectional view of a heart valve holder 60 in accordance with another embodiment engaged with heart valve prosthesis 10. Holder 60 includes holder body 62 having a strut hole 64 therethrough. Strut opening 64 is adapted for receiving primary strut 12. Holder body 62 includes occluder interface surface 66 adapted for engaging occluder 18. Interface surface 66 maintains occluder 18 in the closed position shown in FIG. 3A. A suture opening 70 extends through holder body 62 and receives suture 72. Suture 72 extends through cuff 16 whereby holder 60 is attached to heart valve prosthesis 10 by suture 72 and primary strut 12 extending through opening C4.

Following implantation, holder 60 is removed by cutting suture 72. Holder 60 is then lifted from primary strut 12, thereby freeing occluder 18. Typically, a handle (not shown in FIGS. 3A and 3B) extends from holder 60 in a direction parallel to the plane of the valve orifice body 14 (i.e. a lateral direction) and is used to manipulate valve 10 during implantation.

Figure 4A:
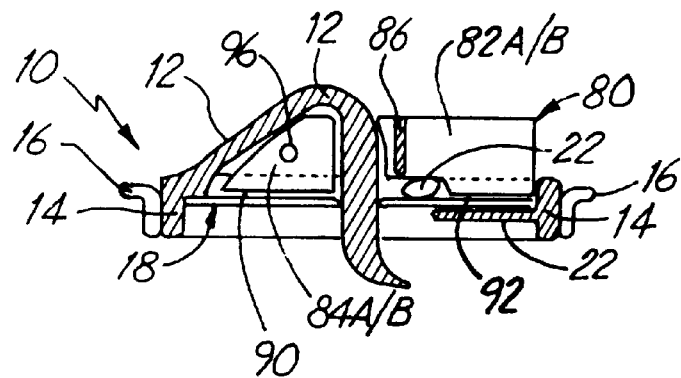
FIG. 4A is a cross sectional view of a holder shown in FIG. 4B taken along line 4B—4B in accordance with another embodiment engaged with a heart valve prosthesis.
Figure 4B:
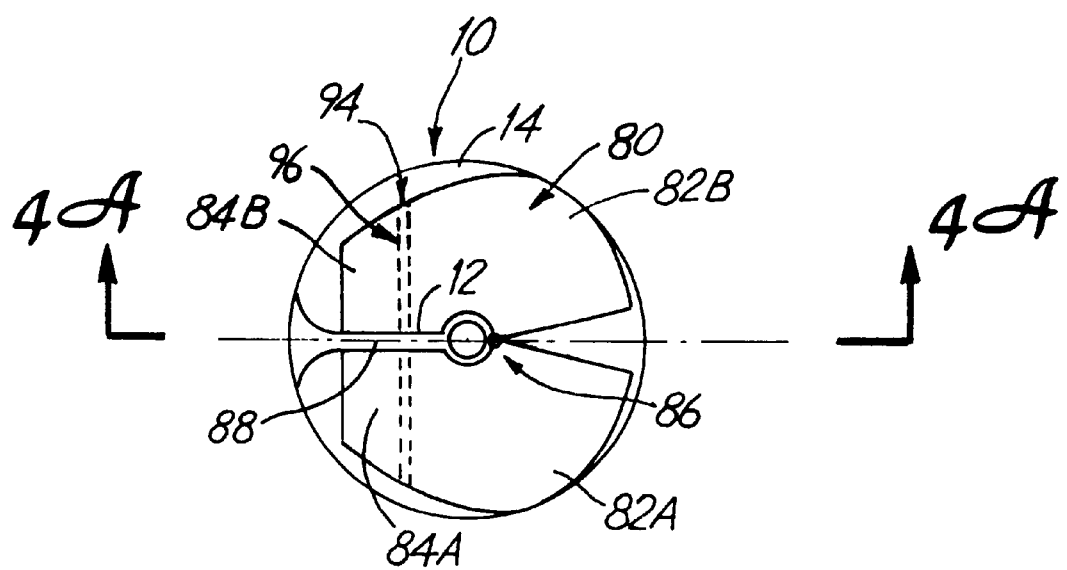
FIG. 4B is a top plan view of the holder of FIG. 4A.

FIG. 4A is a cross sectional view of heart valve holder 80 in accordance with another embodiment engaged with heart valve prosthesis 10. FIG. 4B is a top plan view of holder 80 engaged with heart valve prosthesis 10. Holder 80 includes main body portion 82A and 82B and locking portion 84A and 84B. Main body portions 82A and 82B are connected at hinge 86, and locking portions 84A and 84B separate along the dashed line shown at 88. When holder 80 is in the position shown in FIG. 4B, locking portions 84A and 84B meet along line 88 under primary strut 12. Holder 80 includes surface 90 formed by locking portions 84A and 84B which engages occluder 18. Surface 92 is formed by main body portions 82A and 82B and is adapted for engaging occluder 18.

In the engaging position shown in FIG. 4B, occluder 18 is held in the closed position as shown in FIG. 4A. Locking portions 84A and 84B are held together by a suture 94 which extends through a suture hole 96. Following the implantation of valve 10, holder 80 is removed by cutting suture 94 such that main body portions 82A and 82B are allowed to move together and pivot about hinge 86, causing portions 84A and 84B to move apart thereby freeing heart valve 10 from holder 80. Hinge 86 may be any appropriate hinge mechanism including a flexible material formed integrally with body portions 82A and 82B. Typically an elongated handle, not shown in FIGS. 4A and 4B, extends in a direction parallel to the plane valve orifice body 14 (i.e. a lateral direction) away from valve holder 80 allowing manipulation of valve 10 during implantation.

A variation on the embodiment of holder 80 shown in FIGS. 4A and 4B includes removing hinge 86 such that holder 80 is separable into two halves, one half containing portions 82A and 84A and portions 82B and 84B. In this embodiment, a second attachment mechanism, such as a suture, extends between portions 82A and 82B.

It should be understood that the present invention extends to any variation or embodiment which would be apparent to those skilled in the art. The concepts set forth herein are applicable to any appropriate valve configuration for both aortic and mitral implantation. For example, mitral and aortic configurations have been interchanged in the description set forth herein (compare FIGS. 3A and 3B to FIGS. 1, 2A, 2B, 4A, and 4B). Further, the strut may be positioned in other appropriate locations on the heart valve prosthesis so long as it is accessible to engagement mechanisms and techniques within the scope of the invention. A retaining mechanism may be included in any of the embodiments to secure the occluders during implantation. An elongated handle may be attached to the holders set forth herein for manipulating the heart valve prosthesis during implantation.

Although the present invention has been described with reference to preferred embodiments, workers skilled in the art will recognize that changes may be made in form and detail without departing from the spirit and scope of the invention.

What is claimed is:

1. An apparatus for holding a heart valve prosthesis during implantation, the heart valve prosthesis including a heart valve prosthesis body, a pivotably movable occluder pivotably coupled to a primary strut for carrying the movable occluder, the holding apparatus comprising:

a holder body adapted for abutting the heart valve prosthesis whereby the heart valve prosthesis is in a plane substantially parallel with a plane of the holder body;

a surface on the holder body conforming to the pivotably movable occluder to maintain the pivotably movable occluder in a substantially closed position when the holder body is engaged with the heart valve prosthesis; and an attachment mechanism coupled to the holder body adapted to engage the strut whereby the apparatus is locked between the strut and the heart valve prosthesis.

2. The apparatus of claim 1 wherein the holder body abuts a rim of the prosthesis at an interface.

3. The apparatus of claim 1 wherein the attachment mechanism includes a locking bar extending between the holder body and a portion of the strut.

4. The apparatus of claim 3 wherein the holder body includes a suture hole adjacent the locking bar for receiving a suture therethrough which extends over the locking bar thereby maintaining the locking bar in position between the holder body and the portion of the strut.

5. The apparatus of claim 3 including a spring loaded locking bar cantilever coupling the locking bar to the holder body.

6. The apparatus of claim 1 wherein the holder body includes a suture hole therethrough and the prosthesis includes a suture cuff, the suture hole adapted to receive a suture therethrough to secure the holder body to the prosthesis.

7. The apparatus of claim 1 wherein the attachment mechanism comprises a strut opening formed in the holder body for receiving the strut therethrough.

8. The apparatus of claim 7 wherein the holder body includes a first main body portion and a second main body portion pivotably coupled at a hinge adjacent the strut opening, the first and second main body portions pivotable between an open position in which the strut is free and a closed position in which the strut is secured in the strut opening between the first and second main body portions.

9. The apparatus of claim 8 including a suture releasably coupled to the first and second main body portions to maintain the first and second main body portions in the closed position.

* * * * *